(12) United States Patent
Shabana (10) Patent No.: US 12,207,800 B2
(45) Date of Patent: Jan. 28, 2025

(54) LAPAROSCOPIC CAMERA SYSTEM AND APPARATUS

(71) Applicant: Osama Mossad Ali Shabana, Mansoura (EG)

(72) Inventor: Osama Mossad Ali Shabana, Mansoura (EG)

( * ) Notice: Subject to any disclaimer, the term of this patent is extended or adjusted under 35 U.S.C. 154(b) by 0 days.

(21) Appl. No.: 16/619,120

(22) PCT Filed: May 29, 2018

(86) PCT No.: PCT/EP2018/064122
§ 371 (c)(1),
(2) Date: Dec. 4, 2019

(87) PCT Pub. No.: WO2018/224362
PCT Pub. Date: Dec. 13, 2018

(65) Prior Publication Data
US 2020/0113428 A1 Apr. 16, 2020

(30) Foreign Application Priority Data
Jun. 7, 2017 (GB) .................................. 1709056

(51) Int. Cl.
*A61B 1/313* (2006.01)
*A61B 1/00* (2006.01)
(Continued)

(52) U.S. Cl.
CPC ........ *A61B 1/3132* (2013.01); *A61B 1/00045* (2013.01); *A61B 1/00108* (2013.01);
(Continued)

(58) Field of Classification Search
CPC .............. A61B 1/3132; A61B 1/00045; A61B 1/00108; A61B 1/00142; A61B 1/05;
(Continued)

(56) References Cited

U.S. PATENT DOCUMENTS

| | | | |
|---|---|---|---|
| 5,785,644 | A | 7/1998 | Grabover et al. |
| 2002/0128538 | A1 | 9/2002 | Thompson |

(Continued)

FOREIGN PATENT DOCUMENTS

| | | |
|---|---|---|
| CN | 106880381 A | 6/2017 |
| WO | 2011091566 | 8/2011 |

(Continued)

OTHER PUBLICATIONS

International Search Report of Aug. 29, 2018 for PCT/EP2018/064122.

*Primary Examiner* — Aaron B Fairchild
(74) *Attorney, Agent, or Firm* — Wentsler LLC (57) ABSTRACT

The invention resides in a laparoscope, or camera, for a medical procedure, having a body having a distal end for locating in a patient and a proximal end for handling the laparoscope outside the patient. A camera is provided together with a light source at the distal end. An operable interface is provided adjacent the proximal end, for operating the camera and/or light source. A processor and data storage are located in the body and operable to provide an interface for managing the camera, light source and recording images. The laparoscopic camera can be self-contained such that it is operable without cables or external support devices. It can manage image recording, calibration and storage all within the camera. The invention also resides in a case for use with the laparoscope.

13 Claims, 4 Drawing Sheets

(51) Int. Cl.
*A61B 1/05* (2006.01)
*A61B 1/06* (2006.01)

(52) U.S. Cl.
CPC ............ *A61B 1/00142* (2013.01); *A61B 1/05* (2013.01); *A61B 1/0607* (2013.01); *A61B 1/0615* (2013.01); *A61B 1/0676* (2013.01); *A61B 1/0684* (2013.01)

(58) Field of Classification Search
CPC ... A61B 1/0607; A61B 1/0615; A61B 1/0676; A61B 1/0684; A61B 2017/00212; A61B 2017/00221; A61B 2090/309; A61B 90/361; A61B 17/3421; A61B 2017/00907; A61B 2017/3454; A61B 1/00174; A61B 1/0623; A61B 1/00144; A61B 1/00022; A61B 1/00052; A61B 1/313; A61B 1/00135
USPC ....................................................... 600/109
See application file for complete search history.

(56) References Cited

U.S. PATENT DOCUMENTS

| | | | |
|---|---|---|---|
| 2005/0077688 A1* | 4/2005 | Voegele ............. | A61B 17/3462 277/628 |
| 2008/0064925 A1 | 3/2008 | Gill et al. | |
| 2008/0195128 A1* | 8/2008 | Orbay ................ | A61B 17/320036 600/183 |
| 2008/0221591 A1 | 9/2008 | Farritor et al. | |
| 2010/0016664 A1 | 1/2010 | Viola | |
| 2010/0245549 A1 | 9/2010 | Allen et al. | |
| 2012/0289858 A1* | 11/2012 | Ouyang ............. | A61B 1/00124 600/562 |
| 2013/0128223 A1* | 5/2013 | Wood .................. | A61B 3/1208 351/246 |
| 2013/0253368 A1 | 9/2013 | Are et al. | |
| 2013/0345503 A1* | 12/2013 | Friedrich ........... | A61B 1/00034 600/103 |
| 2014/0005474 A1 | 1/2014 | Farin et al. | |
| 2014/0180007 A1 | 6/2014 | Edidin et al. | |
| 2014/0235942 A1* | 8/2014 | Hellstrom ........... | A61B 1/0615 128/200.26 |
| 2014/0243640 A1* | 8/2014 | O'Dea ................ | A61B 1/3132 600/373 |
| 2014/0276207 A1 | 9/2014 | Ouyang et al. | |
| 2015/0073212 A1* | 3/2015 | Yamazaki ........... | A61B 1/0615 600/179 |
| 2015/0201827 A1 | 7/2015 | Sidar | |
| 2015/0289751 A1* | 10/2015 | Frerck ................ | A61B 1/127 264/293 |
| 2016/0206188 A1 | 7/2016 | Hruska et al. | |
| 2016/0213236 A1 | 7/2016 | Hruska et al. | |
| 2016/0345802 A1* | 12/2016 | Nir ..................... | A61B 1/00045 |
| 2017/0172382 A1 | 6/2017 | Nir et al. | |
| 2018/0218508 A1 | 8/2018 | Lee et al. | |
| 2018/0338670 A1* | 11/2018 | Yamaguchi ........ | G06T 7/514 |
| 2020/0246105 A1* | 8/2020 | Levesque ........... | A61B 1/0615 |

FOREIGN PATENT DOCUMENTS

| | | |
|---|---|---|
| WO | 2012146664 | 11/2012 |
| WO | WO-2016130844 A1 * | 8/2016 ........... A61B 1/3132 |

* cited by examiner

LAPAROSCOPIC CAMERA SYSTEM AND APPARATUS

This invention relates to a laparoscopic vision system and, in particular, to a laparoscopic camera having an imaging device, such as a camera, located at its distal end. More specifically, the invention is directed towards a stand-alone camera, lighting and data recordal apparatus. The invention also extends to kits and systems having such a camera.

Known laparoscopic imaging systems are complex and expensive because of the numerous modules the systems comprise—each module fulfilling a specific function, such as data recordal, providing a light-source, image processing etc. Known systems occupy a lot of space. Only those with adequate training and/or expertise are able to operate and set-up known systems e.g. installing, cleaning and calibrating lighting etc. —before a laparoscopic operation can begin. Known systems have numerous cables and often require dedicated staff to manage the equipment and handle camera cables, light-source cables. Not only do known systems place a burden on an operating procedure because of their complexity but the numerous components and extra staff occupy valuable space in an operating theatre. Further, they provide a plethora of locations where pathogens can be harboured, thus leading to an increased risk of infection.

It is against this background that the present invention has been made. This invention results from efforts to overcome the problems of known laparoscopic systems. Other aims of the invention will be apparent from the following description.

The invention generally resides in a laparoscope that utilises, processes and manages electronic images in a self-contained unit. The laparoscope, by being self-contained, is at least lower cost, more reliable, easier to operate, easier to handle and/or reduces the risk of infection. The laparoscope can be sealed prior to use such that it can be re-used. The laparoscope can operate in stand-alone mode and/or be wirelessly connected to peripheral devices, if required.

According to one aspect, the invention resides in a laparoscope, or camera, for a medical procedure, having a body having a distal end for locating in a patient and a proximal end for handling the laparoscope outside the patient, the laparoscope having: a camera and a light source, located adjacent the distal end; an operable interface, located adjacent the proximal end, for operating the camera and/or light source; and a processor and data storage located in the body, operable to provide an interface for managing the camera, light source and recording images.

The body can have a limb extending therefrom and the processor can reside in the limb. The data storage can be removable from the body. Additionally or alternatively on-board data can be transmitted wirelessly from the laparoscope. The processor can be configured to manage images received from the camera and store them on the data storage or transmit said images. The laparoscope can have an operable interface and the processor can be configured to manage the camera, light source and recording of images.

The distal end can be configured as a trocar. However, it is preferable that the camera of the invention is placed in a trocar in use.

The camera, or imaging device, located at the distal end of the laparoscopic camera is, preferably a high resolution digital camera. The camera can record in high density, or at 4K resolution.

The laparoscopic camera can be self-contained such that it is operable without cables or external support devices. It can manage image recording, calibration and storage all within the camera.

The camera can be positioned on an axis, defined by the proximal and distal ends, and can be maneuverable for enabling the area around the distal end to be viewed. The camera, or image receiving device, can be configured to provide an aligned (zero-degree) view with respect to the axis or can provide a 30-degree view, or can be switchable therebetween. The angle of view can be variable. The angle of view can be variable to provide a complete 360-degree view around the distal end. The view from the imaging camera can be off-axis—to avoid the crease/cutting edge of trocar tip obscuring the view. The light source at the distal end can be positioned to focus upon the centre of the view of the camera imaging device. The light source can be movable in response to camera movement.

A lens can be provided adjacent the distal end, and the lens arranged to co-operate optically with the camera of laparoscope to optimise image quality and/or the range of visibility.

The light source can be positioned offset from the axis defined by the body extending between the ends. A plurality of light sources can be configured on the limb. At least one light source can be positioned at the distal end. At least one light source can be configured on the surface of the limb at the distal end. The light source positioned on the limb at the distal end can be configured to indirectly illuminate a subject to be viewed by the camera i.e. the field of view of the camera can be illuminated by an indirect light source such that the subject is illuminated, at least in part, by incident light.

The light source can be maneuverable for directing emitted light towards the centre of the field of view of the camera. The light source can have a fixed relationship with the camera. A plurality of lights can be provided. The lights can be arranged circumferentially around said axis defined by the limb or by the line-of-sight from the camera sensor.

The operable interface can have a display. The operable interface can have control buttons. The display can be a touch-screen display. The buttons can be provided on the touchscreen display.

The display can be visible through an eyepiece, and buttons can be arranged adjacent the eyepiece to be operable to control the camera and/or the light source while images are being viewed through the eyepiece. Settings, an operations menu, and/or control functions of the interface can be provided via the display.

A plurality of cameras can be provided. Two or more cameras can be provided to enable a 3-dimensional image view to be formed.

The processor can be configured to move the field of view of the camera in response to operation of the interface.

The processor can be configured to adjust at least one of the focus, depth of field or image parameter. The camera and light source can be adapted to see in low-light conditions.

Image parameters can be adjusted by the camera such that at least one or white-balance, contrast, night-vision, infrared imaging can be controlled. Adjustment can be automatic.

The processor can encode the images received by the camera and communicate the image data in real-time, or near real-time with negligible delay, to a monitor for displaying said images and/or a server for recording said images and/or the on-board memory storage on the camera unit.

The laparoscopic camera of the invention can have a communication module configured to wirelessly transmit images and/or data to a remote monitor and/or server. Data, or image data, can be stored and removably located on a memory device located in a slot located at proximal end.

A communication module can be configured to enable remote wireless configuration of at least one of the camera, light source or data.

The control or processing apparatus can occupy the space in the lumen of the limb between the ends. A battery can be positioned in the limb and or distal end. The battery can be charged via a wireless connection, for example via an inductive charging circuit.

The distal end can have a trocar tip and the laparoscope is adapted to provide an opening in a body.

Overall, the laparoscope or camera of the invention can be configured for use inside a trocar or with a trocar tip to enable an opening to be created in a patient. Laparoscopic operations required a patient to be partially inflated to enable a surgeon to have a clear view of the area in which they are operating. The abdomen of a patient expands like a balloon. The apparatus required for such operations must enable a patient to remain inflated. Laparoscopic components, therefore, are configured to compliment these requirements by, for example, being suitably shaped for use with a trocar. It is also to be noted that two or more ports can be created in a patient and that the operating environment for a surgeon is often busy with known laparoscopic apparatus, such as light cables, inflation tubes, camera cables and data cables etc. A compact and simple apparatus, that does not compromise on performance, is preferred.

Although significantly simpler and lower cost compared to known laparoscopic systems—making the laparoscope or camera suitable for single-use—it is preferable that the laparoscope or camera of the invention is re-usable. To support re-use, the laparoscope or camera can be placed inside a sheath or case to keep the unit in a clean, hygienic and hermetically sealing enclosure such that re-use is possible.

A sheath can be provided to enclose a laparoscopic camera as claimed. Said sheath can have a distal end configured to receive the camera and the light source and a proximal end configured to enable a user to view and/or operate the interface. The sheath can be a protective cover. The sheath can be disposable.

In another aspect of the invention, a case is configured to enclose a laparoscopic device or camera. The case can enclose a laparoscopic camera as claimed, said case having a distal end having a trocar tip and a proximal end configured to enable a user to view and/or operate the interface. The case can be adapted to co-operate with the camera and the light source. The case can enclosably and releasably secure the laparoscope therein. To be clear, the laparoscope, or camera, of the invention can be placed in the case, sealed therein, used in an operation, and removed from the case afterwards, such that the camera is re-usable and the case can be disposed of after a single use. The case can temporarily encapsulate the entire laparoscope such that the camera is held in a watertight manner, such as up to IP69, while enabling a user to operate the interface. The case can be shaped to securely or snuggly hold the camera therein.

The case can have a lens adjacent distal end, for co-operation with camera of laparoscope to optimise image quality.

In order that the invention may be more readily understood, reference will now be made, by way of example, to the drawings in which.

In known laparoscopic procedures a trocar 2 is typically placed within a cannula 4 for insertion into a patient. An optical laparoscope not shown is typically placed within the trocar enabling a surgeon to view, via an eye-piece, through the transparent tip of the trocar to the passage of the trocar tip through a patient and into their abdominal cavity. A dedicated light source is connected via a cable to the optical laparoscope. A camera can be placed at the distal end of the optical laparoscope. Images pass from the tip of the trocar through a series of optical lenses and are typically recorded, via a cable, at a remote recording device and/or shown on a screen within the operating theatre.

FIG. 1 shows a laparoscopic camera 10 according to the invention having a body 12 and a limb 14 extending therefrom. The body represents the proximal end 16 that remains outside of a patient's body during an operation. At the tip of the limb 14 is the distal end 18. The distal end 18 of the camera 10 is located within a trocar 2 in place of an optical known laparoscope.

A camera 20 and light source 22 are located at the tip, or distal end 18 of the limb 14 of the camera. Images received at the camera are provided to a motherboard 24 having a processor (not shown) for processing still images or video footage received by the camera. The processor provides the images to a communications board 26 that in turn provides the images to an interface 28. The interface enables the images to be transmitted from the camera 10 via a communication device 30. Additionally, or alternatively, the communications board 26 can present the images to a display 32 located on the camera enabling, preferably on the interface, a user to control the configuration of the camera via control interface 34. Recorded images can additionally or alternatively be obtained from the camera 10 via a memory card slot.

Figure 1A:
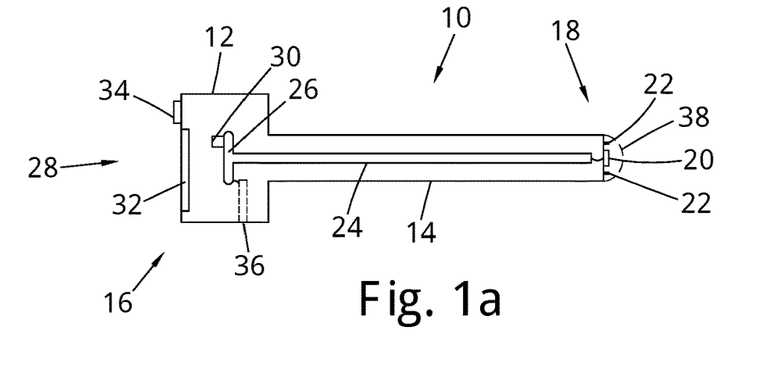
FIG. 1 is sectional view of a camera unit having a camera at a distal end, control within its body and an interface at the proximal end.
Figure 1B:
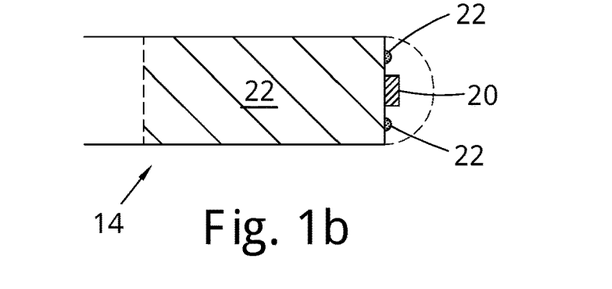
Figure 1C:
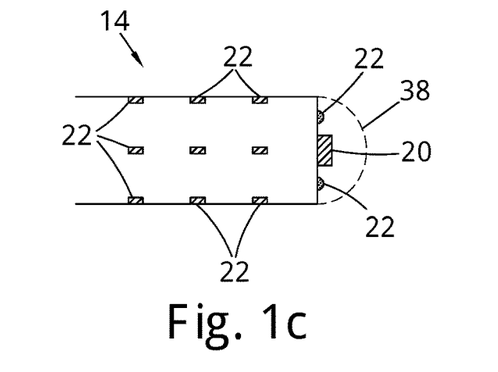
Figure 1D:
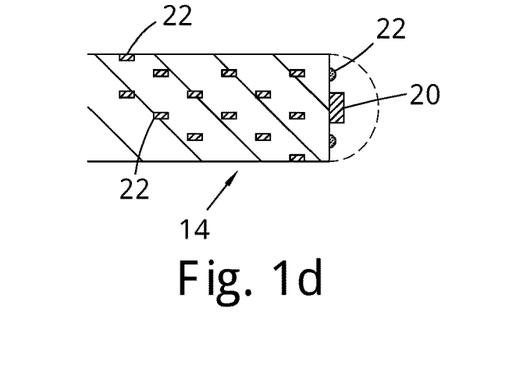

Additionally or alternatively, the light source 22 can be provided on the side walls of the limb 14 around the distal end thereof. Examples are shown in FIGS. 1b, 1c and 1d. In FIG. 1b, the source of the light can be via an light emitting surface or film, which is integrated within or attached to the wall of the limb 14. Such a film would encompass or surround the wall of the limb, at least in part, at the distal end of the camera to project light away from the tip on the limb in all directions. The illuminating film can be a thin film polymer light emitting diode (LED), which is substantially two-dimensional like a sheet of paper. The film can be provided as a single unit, or a plurality of film portions can surround the limb in either circumferential or longitudinal strips. The use of a film enables the diameter of the limb to be minimised i.e. the diameter is not influenced by the packaging of alternative light sources.

Additionally or alternatively, the light source can be a low-profile LED device, similar to the type used at the end of the limb. A plurality of LEDs can be used on each side, at equal distances around the perimeter of the limb, when viewed in cross-section. A row of LEDs can be used. The rows can extend longitudinally along the length of the limb 14 parallel to an axis defined by the limb. A plurality of LEDs can be used, as shown in FIG. 1c. FIG. 1d shows an alternative lighting arrangement that evenly distributes the light by staggering the positions of the light sources around the circumference of the limb. The lines between each light source merely indicate the stepped pattern around the circumference of the limb. The light sources can follow a helical pattern around the surface of the limb. In another alternative layout (not shown), the light sources can be positioned in an asymmetric and non-linear pattern such that patterns of light or shadow are inhibited on the surfaces upon which the light shines.

The light sources 22 on the side of the limb can be selectively illuminated. By way of example, the light source can be illuminated only when it has entered the cavity of a patient in to which the camera 10 is inserted. With the light source provided at a plurality of points around the circumference, in cross-section, of the limb, the light sources can be controlled only to illuminate in the direction that the at camera 20 is focussed upon or is the point of interest of the operator.

By having the light source 22 on the side wall of the limb 14, in addition to the end of the limb, the outward facing light from the device functions to illuminate the space in which the tip of the camera 10, i.e. the distal end of the limb 14. This supplementary light provides additional light to support clear images viewable by the camera 20 and indirectly illuminate the feature that the camera views.

In known systems, laparoscopic cameras are complex because they use a conventional optical laparoscope with a camera located at the proximal end. Many ancillary devices are required to support known cameras, such as a light-source, recording equipment, camera cables and the like—which are all connected to bulky apparatus in an operating theatre via at least one umbilical cord.

Figure 2:
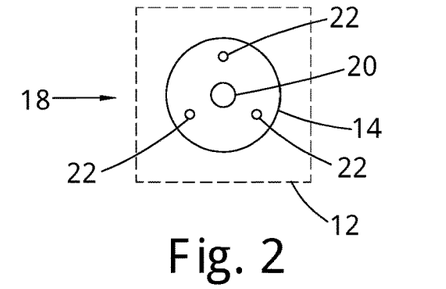
FIG. 2 is an end elevation view of the distal end of the camera in FIG. 1.

FIG. 2 shows an end elevation view of the camera 10 looking upon the distal end 18 such that the footprint of the body 12 can be seen with the circular body of the limb 14 having the camera 20 and light sources 22 located thereabout. A lens 38 can be provided over the camera to optimise the images received by the camera. Three light sources, such as light emitting diodes, or LEDs, are shown by way of example, although any number of LEDs can be provided.

Figure 3:
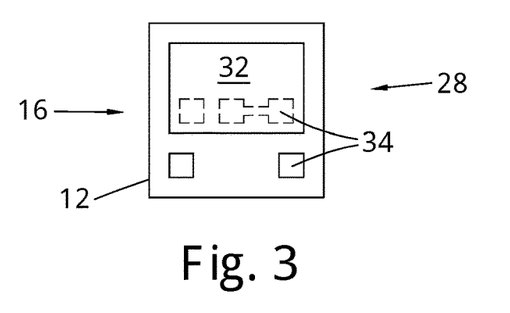
FIG. 3 is an end elevation view of the proximal end of the camera in FIG. 1.

FIG. 3 shows an end elevation view of the body 12 including the interface 28 having a display 32 and control interface 34. The display can be a touch-screen display having additional control interface buttons on the display.

Figure 4:
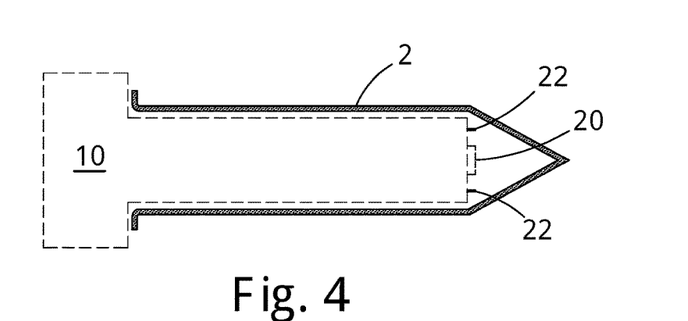
FIG. 4 shows an illustration of the camera of FIG. 1 located in a trocar.

FIG. 4 shows a cross-sectional representation of the camera 10 located within a trocar 2. The camera 10 is a reusable unit and is preferably enclosable within a sheath (not shown) in use, and the camera 10 would be enclosed within a sheath before being placed within the trocar 2. The sheath is transparent, such that it does not impede upon the images received by the camera.

Figure 5:
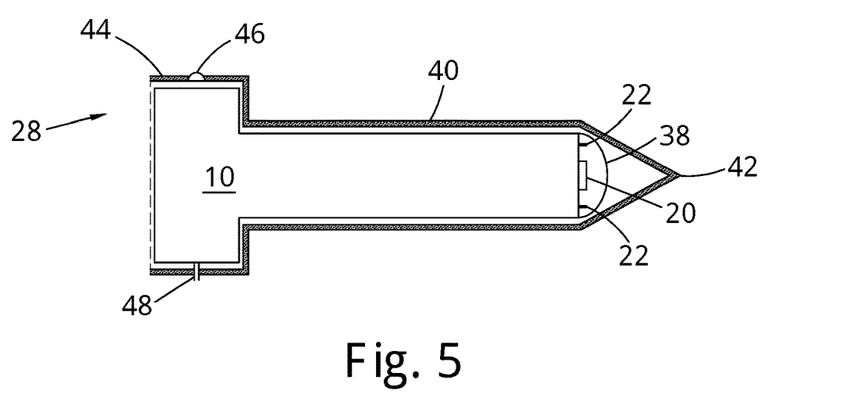
FIG. 5 shows an illustration of the camera of FIG. 1 located in a trocar, said trocar having a lid to provide an enclosure for the camera.

FIG. 5 shows a laparoscopic camera 10 according to the invention located within a case 40. The case is typically formed from transparent plastic. The case has a trocar tip 42 and a lid 44 that can be opened about a hinge 46 and secured by a lock 48 such that the camera 10 can be sealed, preferably hermetically sealed, within the case 40. In this configuration, the camera 10 is reusable while the case 40 is for single-use. The lid 44 is configured to enable full operability of the interface 28 and control interface 34, and for the display to be viewed.

Figure 6:
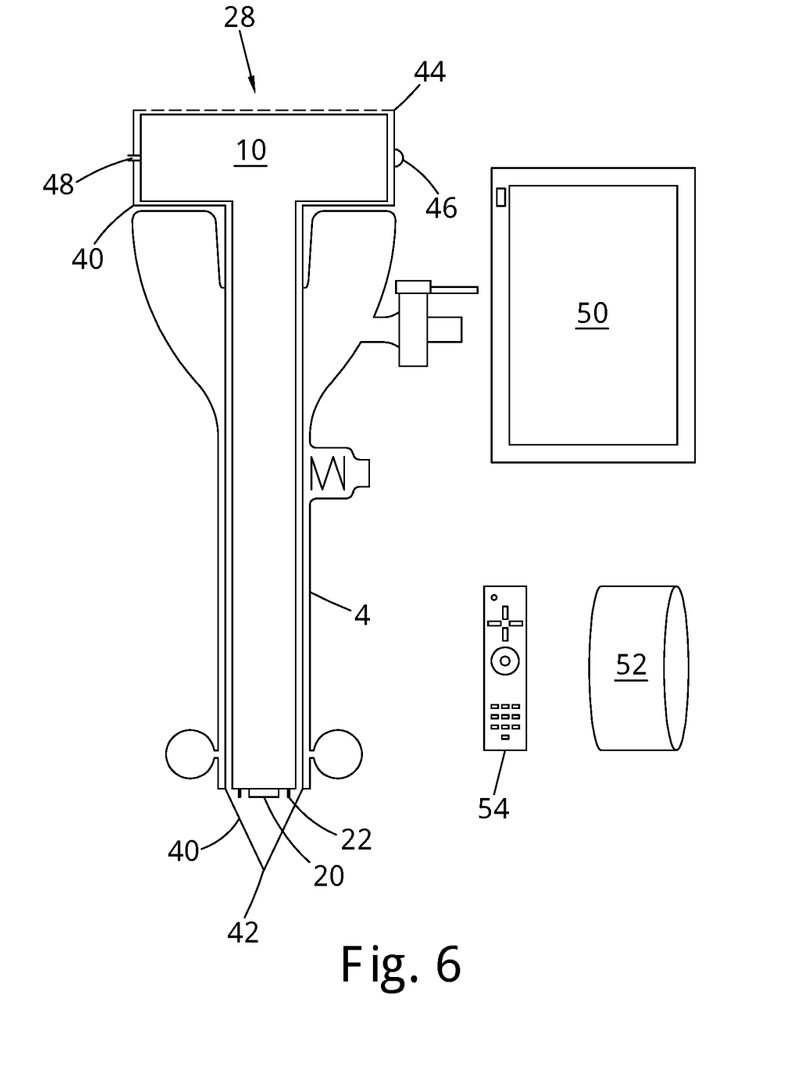
FIG. 6 shows a camera system having the camera and enclosure of FIG. 5 located in a cannula for insertion to a patient, monitor, server and remote controller.

FIG. 6 represents a typical laparoscopic system according to the invention in which a laparoscopic camera 10 is located within a case 40 and placed within a cannula 4. Images received from the camera 20 would be processed on the motherboard 24 before being provided to the communications board 26 and interface 28 of the camera 10. A surgeon would have full control of the camera 10 via the interface 28 using the control interface 34 and display 32. The camera 10 is self-contained and can process images received by the camera 20, store said images and allow images to be recorded and taken from the camera 10 via the memory card 36. Additionally or alternatively, the camera can transmit via the communication device 30 images and data to a monitor 50 and/or a remote server 52. A remote control 54 can be used to operate at least one of the camera 10, monitor 50 or server 52. The camera 10, monitor 50, remote 54 and server 52 can communicate and transmit date wirelessly therebetween.

In operation, the camera 10 provide a view on the display 32 and/or monitor 50 through the tip of a trocar 2 or the tip of the case 40 in which it is placed. In this way a surgeon can see the surgical site where an opening is to be made.

The camera 10 provides its own illumination and can automatically adjust the focus, contrast and/or white-balance to optimise the view of the site for the surgeon. Infra-red light sources and image sensing can additionally or alternatively be provided.

The hand-held camera 10 can be fully configured and calibrated by directly operating the interface 28 of the camera. In subsequent use, images and video can be recorded and stored upon the device and process for removal via a memory card or wireless transmission via the communication device 30. No additional cables, light source or remote monitor are required because the camera is self-contained and a surgeon would have complete operable control of the camera via the interface 28.

By way of example, in use the interface 28 can be used to adjust the field of view of the camera via the buttons on the control interface 34 or via a control interface 34 located directly on the display 32. Image parameters such as white balance, contrast, or modes of vision can be managed automatically by the processor upon the motherboard 24 or adjusted by a surgeon via the interface.

The camera and the light source are able to present images representing the view from the distal end 18 in either full colour i.e. visible light or in infrared.

Figure 7:
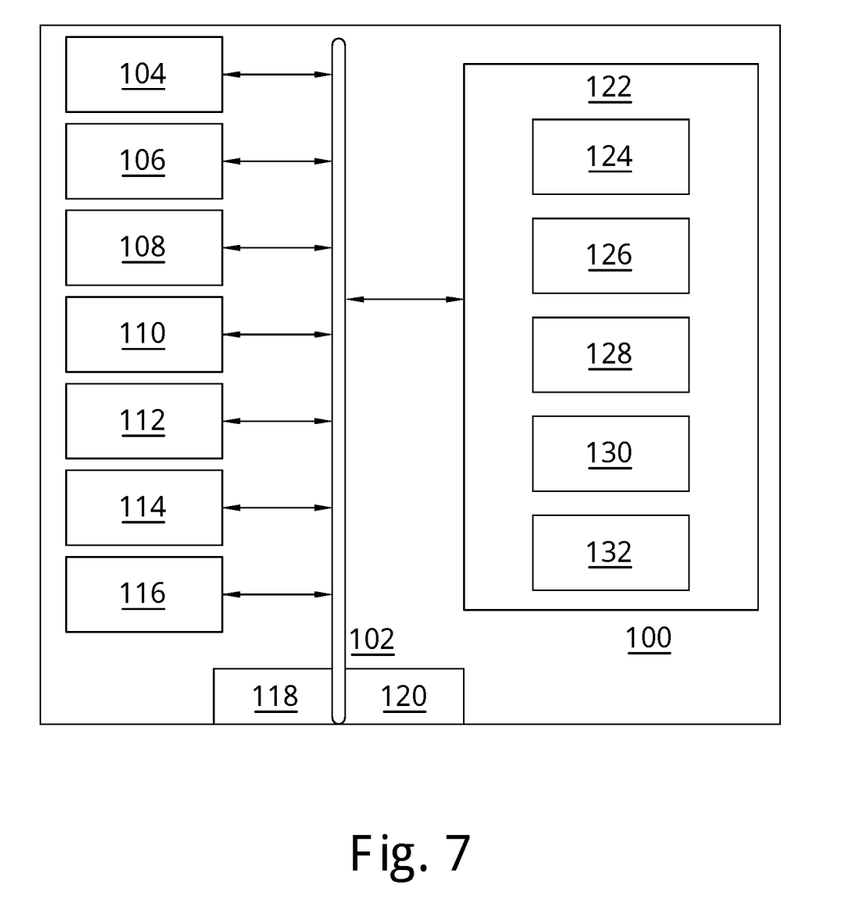
FIG. 7 shows a schematic view of a system residing within a camera according to FIG. 1.

The camera sensor 20 and the light source 22 can be fixed to centre received images on objects aligned with the longitudinal axis of the limb 14. Alternatively, the camera sensor 20 and the light source 22 located at the distal end 18 can be located on a movable or articulated actuator or other such movable device (not shown). The actuator is operable via the interface 34 or control 54 to change the camera view such that it can pan around said axis enabling a surgeon to adjust the camera view and see around the trocar tip. FIG. 7 is an example of the system residing within the camera 10 thus enabling the camera to be operable as a stand-alone unit, independently of remote devices. To be clear, the laparoscopic camera of the invention can operate to display, manage and record images as a self-contained unit without the need of any external devices or connections such as cables, light source, camera control units or monitors. A system 100 residing within the camera 10 includes a number of components distributed between the motherboard 24 and the communications board 26. The device 100 includes a bus 102, at least one processor 104, at least one communication port 106, a main memory 108 and/or a removable storage media 110 typically a memory card within a memory card slot 36, a read-only memory 112 and a random access memory 114. The system also includes a battery 116. The port 106 can be complimented by input means 118 and an output connection 120.

The processor 104 can be any such device such as but not limited to an Intel®, AMD®, or ARM processor. The processor may specifically be dedicated to the system and camera 10. The port 106 can be a wired connection, such as an RS232 connection, or a Bluetooth connection or any such wireless connection. The port can be configured to communicate on a network such as a Local Area Network LAN, Wide Area Network WAN, or any network to which the camera 10 connects.

The system 100 residing within the camera 10 can include an image processor 122 to receive data from the camera 20 and process the signals received therefrom. The image processor can include a lighting controller 124 that can adjust the colour and/or intensity of the light emitted from the light source 22. The image processor can also include a camera configuration module 126 for adjusting at least one of the focus or white balance of the image received, by way of example. A video control module 128 can be provided to manage, for example, the rate at which video is recorded. An image mode module 130 can be provided to enable the operating mode of the camera 20 to be switched between, for example, recording image stills, recording video, recording colour images or recording images using night-vision, such as in infrared mode.

Finally, a controller 132 can be provided to enable changes to the physical position to the camera 20 located at the tip, which can alternatively be operable via an actuator not shown such that the view from the camera can be turned such that full hemispherical vision can be achieved by the camera.

The camera 10 can include one or more specific features that optimise the performance and usability.

By way of example, the camera 10 can be positioned on an axis, said axis defined as a longitudinal axis extending centrally within the limb 14 between the distal end 18 and proximal end 16 of the camera. The camera 20 can be maneuverable for enabling the area around the distal end 16 to be viewed. The tip of the limb 14 can be articulated. Additionally or alternatively the camera 20 and light source 22 can be positioned on an actuator enabling the rotation and angular adjustment of the camera 20.

The camera has been described as lying on the axis, but can, alternatively, be positioned off-axis to avoid an image being obscured by the crease or cutting edge of a trocar tip obscuring the view.

Light passing through a transparent trocar tip 42 can be optically adjusted due to the refractive nature of the trocar tip, which functions as a lens. The camera 10 can be provided with a lens 38 that functions to compensate for the distortion caused by the trocar tip and, therefore, improves upon the light received by the camera 20. Image adjustment can additionally or alternatively be made by an image processor to compensate for image distortion. The light source 22 can be actuatable with the camera such that light emitted from the light source is focussed towards the centre of the field of view of the camera.

The present invention has been described above purely by way of example, and modifications can be made within the spirit of the invention, which extends to equivalents of the features described. The invention also consists in any individual features described or implicit herein or shown or implicit in the drawings or any combination of any such features or any generalisation of any such features or combination.

The invention claimed is:

1. A laparoscope for a medical procedure for use inside a trocar or with a trocar tip to enable an opening to be created in a patient and provide an air-tight seal so a body of said patient can be pumped with air, the laparoscope comprising:
   a body having a distal end for locating in said patient and a proximal end for handling said laparoscope outside said patient, and a limb extending therebetween to define a longitudinal axis, and wherein said limb has a uniform circular cross-section along its entire length;
   at least one camera located adjacent to said distal end of said body, wherein said camera is positioned on said longitudinal axis and arranged to provide an off-axis field of view;
   at least one light source comprising multiple evenly spaced light sources arranged at said limb's distal end arranged circumferentially around said longitudinal axis defined by said limb and evenly distributed by staggering the positions of said multiple evenly spaced light sources around the circumference of said limb;
   at least one operable interface having a display located adjacent to said proximal end of said body, said at least one operable interface containing controls for operating said at least one camera, said a least one light source, or combinations thereof; and
   at least one processor and at least one data storage device located internal of said body operable to provide a control interface for managing said at least one camera said at least one light source, or combinations thereof, and further operable for recording at least one image from said camera.

2. The laparoscope according to claim 1, wherein said multiple evenly spaced light sources are each a thin film polymer light emitting diode (LED) film, a plurality of low-profile light emitting diodes, or a combination thereof.

3. The laparoscope according to claim 1, wherein said at least one processor is configured to move said field of view of said at least one camera in response to operation of said at least one operable interface.

4. The laparoscope according to claim 1, wherein said at least one processor is configured to adjust at least one of a focus, a depth of field, at least one image parameter, or combinations thereof.

5. The laparoscope according to claim 1, wherein said at least one camera and said at least one light source are adapted to see in low-light conditions.

6. The laparoscope according to claim 1, further comprising at least one communication module configured to wirelessly transmit at least one image, data, or combinations thereof, to at least one remote display, at least one remote monitor, at least one server, or combinations thereof.

7. The laparoscope according to claim 6, wherein said at least one communication module is configured to enable remote wireless configuration of at least one of said at least one camera, said at least one light source, said at least one image, said data, or combinations thereof.

8. The laparoscope according to claim 1, wherein said data storage device located in said body of said laparoscope is capable of managing image recording, calibration, and storage all within said at least one camera.

9. The laparoscope according to claim 1, wherein said at least one light source is configured to indirectly illuminate said camera's field of view in all directions to enable visualization about said distal end of said body during a surgical procedure.

10. The laparoscope according to claim 1, wherein said multiple evenly spaced light sources are selectively operable to adjust illumination intensity of said at least one camera's said field of view to compensate for variations in the lighting conditions in all directions about said distal end of said body.

11. A laparoscope for a medical procedure, said laparoscope comprising:
- a body having a distal end for locating in a patient and a proximal end for handling the laparoscope outside the patient;
- at least one camera located adjacent the distal end of said body, wherein said camera is positioned on said longitudinal axis and arranged to provide an off-axis field of view;
- at least one light source illuminating said camera's field of view;
- at least one operable interface having at least one display and at least one control button located adjacent to said proximal end of said body, said at least control button configure for operating said at least one camera, said at least one light source, or combinations thereof, wherein said body of said laparoscope includes said at least one operable interface;
- at least one processor and at least one data storage device located internal of said body operable to provide an interface for managing said at least one camera, said at least one light source, or combinations thereof, and further operable for recording at least one image from said at least one camera; and
- at least one case for single-use having a distal end having a trocar tip and a proximal end having at least one lid configured to hermetically seal said at least one camera within said at least one case, in use, wherein said at least one lid is configured to enable a user to view and/or operate said operable interface, wherein said at least one camera is configured to provide a view on said at least one display through said tip of said at least one case in which it is placed thus enabling a surgeon to see the surgical site where an opening is to be made
- wherein said at least one light source comprises multiple evenly spaced light sources arranged at said limb's distal end arranged circumferentially around said longitudinal axis defined by said limb and evenly distributed by staggering the positions of said multiple evenly spaced light sources around the circumference of said limb.

12. The laparoscope according to claim 11, wherein said at least one light source is configured to indirectly illuminate said camera's field of view in all directions to enable visualization about said distal end of said body during a surgical procedure.

13. The laparoscope according to claim 11, wherein said multiple evenly spaced light sources are selectively operable to adjust illumination intensity of said at least one camera's said field of view to compensate for variations in the lighting conditions in all directions about said distal end of said body.

* * * * *